US007438915B2

(12) United States Patent
Lillehoj

(10) Patent No.: US 7,438,915 B2
(45) Date of Patent: Oct. 21, 2008

(54) **IMMUNOPOTENTIATING EFFECT OF A *FOMITELLA FRAXINEA*-DERIVED LECTIN ON CHICKEN IMMUNITY AND RESISTANCE TO COCCIDIOSIS**

(75) Inventor: Hyun S. Lillehoj, West Friendship, MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 12 days.

(21) Appl. No.: 11/203,587

(22) Filed: Aug. 10, 2005

(65) Prior Publication Data

US 2007/0036817 A1      Feb. 15, 2007

(51) Int. Cl.
*A61K 39/00*   (2006.01)
*C07K 14/44*   (2006.01)

(52) U.S. Cl. ..................... 424/191.1; 530/395
(58) Field of Classification Search ........................ None
See application file for complete search history.

(56) References Cited

U.S. PATENT DOCUMENTS 4,742,046 A * 5/1988 Bliah ............................ 514/8

(Continued)

FOREIGN PATENT DOCUMENTS

KR      1019970011556    * 12/1997

(Continued)

OTHER PUBLICATIONS

Matsumoto, Hanako et al, Biochimica et Biophysica ACTA, vol. 1526, pp. 37-43, 2001 Screening of a unique lectin from 16 cultivable mushrooms with hybrid glycoprotein and neoproteoglycan probes and purification of a novel N-acetylglucosamine-specific lectin from *Oudemansiella platyphylla* fruiting body.*

(Continued)

*Primary Examiner*—Mark Navarro
*Assistant Examiner*—Ginny Portner
(74) *Attorney, Agent, or Firm*—John D. Fado; Evelyn M. Rabin

(57) ABSTRACT

This study reports a novel immunopotentiating effect of a lectin (FFrL) extracted from the mushroom *Fomitella fraxinea* on poultry cell-mediated immunity and poultry coccidiosis. We describe the extraction of FFrL, its in vitro mitogenic activity and in vivo protection against an oral challenge infection with *Eimeria acervulina*. When tested on several cell types, crude FFrL agglutinated mouse erythrocytes and thymocytes and also various other cells including murine and human cell lines. However, crude FFrL did not agglutinate human A, B, AB, or O erythrocytes. FFrL showed a potent mitogenic activity on chicken splenic lymphocytes where at lower concentrations, crude FFrL exerted stronger mitogenic activity than Con A, a well-known potent mitogen for T lymphocytes. Further, FFrL significantly induced ($P<0.05$) nitric oxide secretion in HD11 cells, an established macrophage cell line, and suppressed ($P<0.05$) RP9 tumor cell growth, both, in a dose-dependent fashion. When injected into eighteen-day-old chicken embryos followed by an oral *E. acervulina* challenge infection, FFrL-treatment significantly protected chickens against weight loss associated with coccidiosis ($P<0.05$). Injecting embryos with FFrL also resulted in significant reduction in oocyst shedding as compared to the control saline-injected birds ($P<0.05$). The results of this study demonstrate that FFrL is an effective growth-promoting and immunostimulating agent in poultry during coccidiosis.

12 Claims, 6 Drawing Sheets

U.S. PATENT DOCUMENTS

2003/0092109 A1* 5/2003 Goldstein et al. .......... 435/69.1
2005/0064391 A1* 3/2005 Segal et al. ................ 435/5

FOREIGN PATENT DOCUMENTS

| KR | 2002081824 | * | 10/2002 |
| KR | 1020020081824 | * | 10/2002 |
| KR | 2003030312 A | * | 4/2003 |

OTHER PUBLICATIONS

Bae, Man-Jong et al, Korean Journal of Mycology, vol. 24(2), pp. 142-148 1996, Studies on immunmodulating function of componets separted from higher fungi (English abstract only & Korean articl).*
Kim, YK et al, Korean Journal of Animal Science, vol. 37(6), pp. 633-638, 1995, Effect of fungal additive on the lactational response of dairy cows (English abstract only).*
Pons, Luis, Dec. 8, 2006, ARS, US Department of Agriculture, Mushrooms have a future in Fighting a fowl parasite.*
Sreter, T et al, Folia Parasitol (Praha), 1997, vol. 44(1), pp. 77-80, Attempts to immunize against *Cryptosporidium baileyi* with *C. parvum* oocysts and Paracox vaccine (abstract only).*
Hornok, S et al, Veterinary Parasitology, vol. 89, 2000, pp. 313-319, Influence of an in ovo administered *Cryptosporidium baileyi* oocyst extract on the course of homologous infection.*
Blake, Damer P et al, Avaian Pathology, Dec. 2005, vol. 34(6), pp. 489-494, The influence of immunizing dose size and schedule on immunity to subsequenct challenge with antigenically distinct strains of *Eimeria maxima*.*
Kopko, SH et al, Poultry Science, vol. 79, pp. 336-342, 2000, Responses of Chickens to a Recombinant Refractile Body antigen of *Eimeria tenella* adminsitered using various immunizing strategies.*
Jenkins, Mark C. International Journal of Parasitology, vol. 28, pp. 111-1119, 1998, Progress on developing a recombinat coccidiosis vaccine.*
Smith, Adrian L et al, Infection and Immunity, vol. 70(5), pp. 2472-2479, May 2002, Antigenic Diversity in *Eimeria maxima* and the in fluence of Host Genetics and immunization Schedule on Cross-Protective immunity.*
Boslego, John W et al, Capter 17, pp. 211-223, In Vaccines and Immunotherapy 1991, Pergamon Press.*
Ellis, Ronald W, Ph.D, Chapet 29, New Technologies for Making Vaccines, pp. 568-575, in Vaccines Plotkin & Mortimer 1988.*
Dalloul, RA et al, Immunopotentiating effect of a *Fomitella fraxinea* derived lectin on chicken immunity and resistance to Coccidiosis, Poultry Science, 2006, vol. 85, pp. 446-451.*
Yagi, Fumio et al, Mycoscience, vol. 41, pp. 323-330, 2000, Hemgglutinins (lectins) in fruit bodies of Japanes higher fungi.*
JSCC On-Line Database Srains MAFF420008 *Perenniporia fraxinea*, synonym *Fomitella fraxinea*.*
Guo, FC et al, Effects of Mushroom and Herb polysaccharides on Cellular and Humoral Immune responses of *Eimeria tenella* infected chickens, Poultry Science, 2004, vol. 83, pp. 1124-1132.*
Guo, FC et al, Effects of Mushroom and Herb polysaccharides as alternatives for an antibiotic on the cecal microbial ecosystem in boiler chickens, 2004, Poultry Science, vol. 83, pp. 175-182.*
Dalloul, Rami A. et al., "In ovo administration of CpG oligodeoxynucleotides and the recombinant microneme protein MIC2 protects against *Eimeria* infections," *Vaccine*, 2005, vol. 23, pp. 3108-3113.
Ding, Xicheng et al., "Protective Immunity against *Eimeria acervulina* following In Ovo Immunization with a Recombinant Subunit Vaccine and Cytokine Genes," *American Society for Microbiology*, Dec. 2004, vol. 72, No. 12, pp. 6939-6944.

* cited by examiner

IMMUNOPOTENTIATING EFFECT OF A *FOMITELLA FRAXINEA*-DERIVED LECTIN ON CHICKEN IMMUNITY AND RESISTANCE TO COCCIDIOSIS

BACKGROUND OF THE INVENTION

1. Field of the Invention

The U.S. poultry industry has experienced important economic losses as a result of avian coccidiosis, the major parasitic disease of poultry. This invention relates to a mushroom lectin extracted from *Fomitella fraxinea*, FFrL, and pharmaceutical compositions comprising FFrL which have immunopotentiating effects on poultry cell-mediated immunity and can be used in a strategy to control coccidiosis in the poultry supply.

2. Description of the Relevant Art

Mushrooms and mushroom lectins have recently gained significant attention in medical research due to their immunoenhancing effects and their demonstrated potential in promoting health (Borchers et al. 2004. *Exp. Biol. Med.* 229:393-406). Lectins are carbohydrate-binding proteins or glycoproteins of non-immune origins, which have the ability to induce cell agglutination (Goldstein et al. 1980. *Nature* 285: 66). They have been found in diverse living organisms including animals, plants and microorganisms (Cammue et al. 1985. *Eur. J. Biochem.* 148:315-322; Suzuki, Y. 1985. *Bull. Jap. Soc. Sci. Fish.* 51:2083; Avichezer and Gilboa-Garber. 1991. *Toxicon* 29:1305-1313). Lately, there has been a growing interest in lectins specifically, largely due to the discovery that some lectins exert various important biological activities including immunomodulatory activities (Ribéreau-Gayon et al. 1996. *Cancer Lett.* 109: 33-38; Wang et al. 1996. *Immunopharmacology* 31:205-211; She et al. 1998. *Biochem. Biophys. Res. Commun.* 247:106-111; Lima et al. 1999. *Immunopharmacology* 41:147-155; Suvachittanont and Jaranchavanapet. 2000. *Planta Medica* 66:699-704; Ho et al. 2004. *Biochem. Biophys. Acta* 1671:9-17), anti-proliferative/anti-tumor activities (Wang et al., supra; Abdullaev and de Mejia. 1997. *Toxins* 5:157-163; Yoon et al. 1999. *Cancer Lett.* 136:33-40; Karasaki et al. 2001. *Food Res. Int.* 34:7-13; Zhao et al. 2003. *Biochem. J.* 374:321-327; Ngai and Ng. 2004. *Biochem. Biophys. Res. Commun.* 314:988-993), antifungal activities (Gozia et al. 1993. *FEBS Lett.* 370:245-249; Ye et al. 2001. *J. Protein Chem.* 20:367-375) and anti-viral activities (Marchetti et al. 1995. *Res. Virol.* 146:211-215; Ye et al., supra). Although many mushroom lectins have been isolated and characterized (Guillot and Konska. 1997. *Biochem. Syst. Ecol.* 25:203-230), only some of them have been shown to possess immunomodulatory and anti-tumor activity (Wang et al. 1996, supra; Wang et al. 2002. *Life Sci.* 70:877-885; She et al., supra). More recently, some mushroom extracts were shown to have immunoenhancing potential in chickens (Guo et al. 2004. *Poult. Sci.* 83:1124-1132; Guo et al., 2005. *Avian Dis.* 49:70-73) particularly during coccidiosis.

Avian coccidiosis is the major parasitic disease of poultry with substantial economic burden to the industry. In-feed medication for prevention and treatment of coccidiosis contributes to a major portion of the economic costs. Additional economic losses associated with coccidiosis are mortality, malabsorption, inefficient feed utilization and impaired growth rate in broilers, and a temporary reduction of egg production in layers. Coccidiosis is caused by several apicomplexan parasites of the genus *Eimeria* that infect the intestinal tract and are transmitted between birds via ingestion of infective oocysts during feeding. While natural infection and live oocyst vaccination with *Eimeria* spp. induces immunity, disease control remains largely dependent on routine use of anti-coccidial drugs (Lillehoj et al., 2004. *Poult. Sci.* 83:611-623; Dalloul and Lillehoj. 2005. *Avian Dis.* 49:1-8). The poultry industry in the United States as well as worldwide has relied heavily upon prophylactic chemotherapy resulting in the development of resistant strains of *Eimeria* to all introduced anticoccidial drugs (Chapman, H. D. 1997. *Avian Pathol.* 26:221-244). Therefore, the lack of efficient vaccines, the increasing incidence of drug resistant strains, escalating public anxiety over chemical residues in meat and eggs as well as regulatory bans of growth promoting drugs in poultry production, mandate the development of alternative control methods.

Therefore, recent research has focused on the development of alternative disease control strategies including the introduction of alternative prevention/treatment measures such as non-chemical feed supplements (Dalloul et al. 2003a. *Poult. Sci.* 82: 62-66; Dalloul et al. 2003b. *Avian Dis.* 47:1313-1320), novel and effective vaccines, including recombinant vaccines (Ding et al. 2004. *Infect. Immun.* 72:6939-6944; Ding et al. 2005. *Vaccine* 23:3733-3740; Min et al. 2003. *Vaccine* 20:267-274; Lillehoj et al., 2004, supra; Lillehoj et al., 2005. *Avian Dis.* 49:112-117 and live vaccines (Weber et al. 2004. *Poult. Sci.* 83:392-399); and other immunization strategies such as the use of CpG oligodeoxynucleotides (Dalloul et al. 2005. *Vaccine* 23:3108-3113) and mushroom and herb extracts (Guo et al. 2004 and 2005, supra).

There continues to be a need for alternative strategies to control avian coccidiosis caused by *Eimeria*. We have investigated the effects of a mushroom-derived lectin in inducing immunoprotection against an *Eimeria* challenge.

SUMMARY OF THE INVENTION

We have extracted a lectin from the mushroom *Fomitella fraxinea* and discovered that the lectin has immunopotentiating effects that are useful in the control of avian coccidiosis.

In accordance with this discovery, it is an object of the invention to provide an isolated lectin, FFrL, extracted from *Fomitella fraxinea*.

It is a further object of the invention to provide an immunostimulating composition containing FFrL for stimulating non-specific cell mediated immunity against diseases in poultry caused by viruses, bacteria, or parasites.

It is a still further object of the invention to provide an immunostimulating composition containing FFrL for controlling avian coccidiosis in poultry, wherein the immunostimulating composition comprises a physiologically acceptable carrier and an effective immunostimulating amount of FFrL.

It is another object of the invention to provide a method for preventing or minimizing the development of coccidiosis in poultry.

A further object of the present invention is to utilize FFrL as an immunostimulant for delivery to poultry in ovo.

Yet another object of the present invention is to utilize FFrL as an immunostimulant for providing protection against diseases in poultry without the need for additional immunization steps or vaccines.

An additional object of the present invention is to utilize FFrL as an immunostimulant for providing protection against diseases in poultry together with additional immunization steps and/or vaccines.

It is an additional object of the present invention is to administer FFrL with adjuvants such as probiotics, oligodeoxynucleotides, cytokines, and herbs to potentiate the effect of the mushroom extract.

Also part of this invention is a kit, comprising an FFrL-containing composition for preventing or minimizing the development of coccidiosis in poultry; and instructions for the use of the kit.

Other objects and advantages of this invention will become readily apparent from the ensuing description.

DETAILED DESCRIPTION OF THE INVENTION

Figure 1:
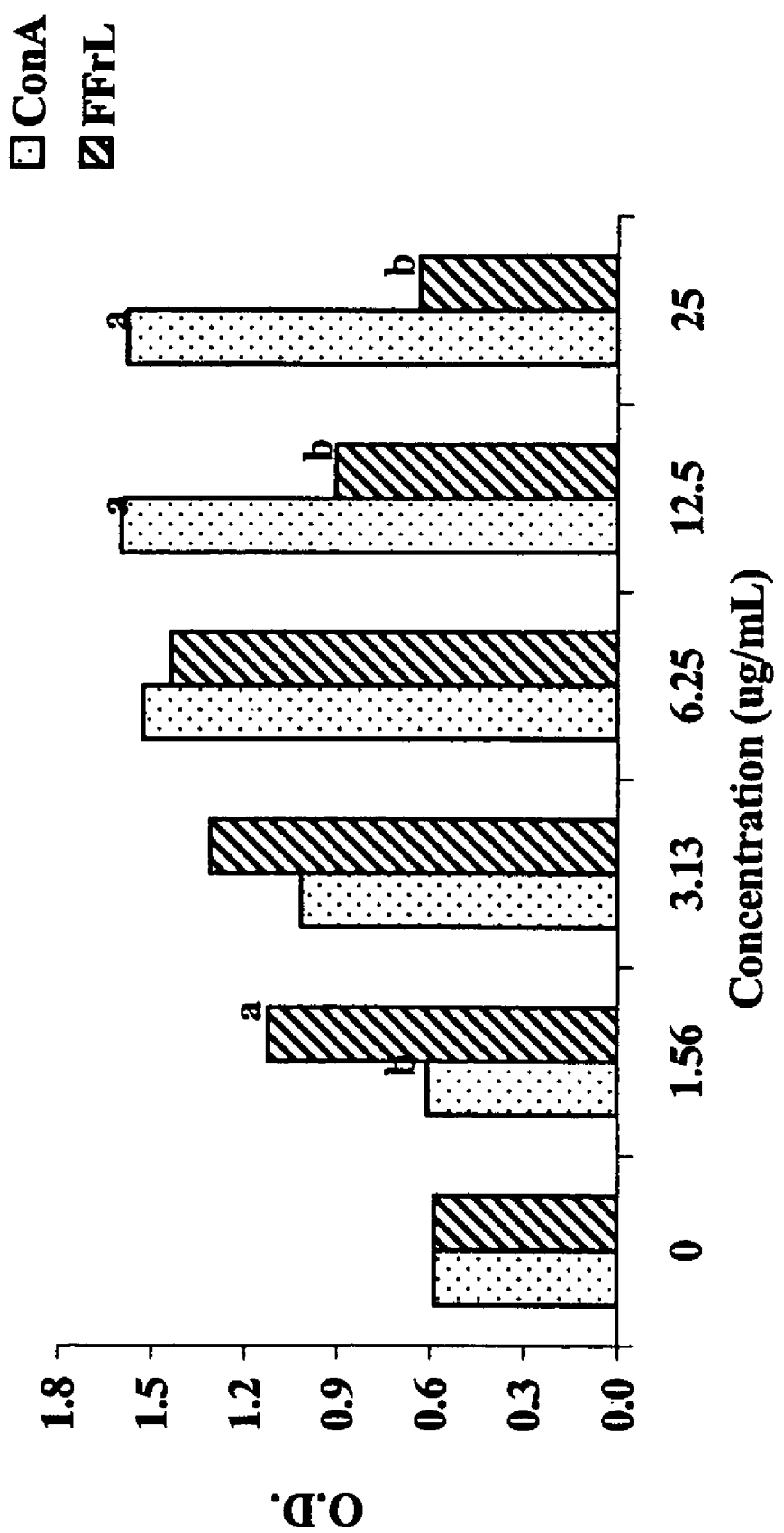
FIG. 1 shows mitogenic activity of crude FFrL on the chicken splenic lymphocytes. Spleen lymphocytes were prepared and co-cultured with the stimulants at 42° C. for 48 h in a 5% $CO_2$ atmosphere; cell growth was then assessed by the XTT method (Absorbance was read at 450 nm). $^{a-b}$ P<0.05; error bars=SE.

The present invention relates generally to an agent useful for stimulating or potentiating the immune system of a host animal, and more particularly, to compositions and methods for providing stimulation to the immune system of a host animal. The present invention is directed to the use of the immunopotentiator FFrL to stimulate, or potentiate, the immune system of a host animal. More particularly, the invention relates to immunopotentiating compositions, and to a method for potentiating the immune system of a host animal having an immune system in need of potentiating, by administering to the host animal a composition comprising an effective amount of the immunopotentiating lectin FFrL. We describe the immunopotentiating effects of a mushroom lectin (FFrL), extracted from *Fomitella fraxinea*, on poultry cell-mediated immunity and subsequent protection of the poultry supply against coccidiosis. A strategy to control coccidiosis would be advantageous and valuable for the poultry industry.

A primary function of the immune system is to protect the animal against the deleterious effects of pathogens. One type of immune system response to pathogens is a cell-mediated immune response which protects the animal against invasion by pathogens such as bacteria, viruses, and parasites. A cell-mediated immune response involves T lymphocytes and in addition other cells, for example, B lymphocytes, macrophages, dendritic cells, and polymorphic nuclear cells. The presence of an invading pathogen results in the expansion of two types of T lymphocytes: cytotoxic T cells, that can destroy the invading pathogen, and helper T cells, that enhance the body's defenses against the invader. Assays that can be used to determine and measure T cell and B cell activation are well known and used in the art. Two patents (U.S. Pat. Nos. 5,785,973 and 5,601,831) which discuss B and T cell assays used to determine if B or T cells have become specifically activated are hereby incorporated by reference.

The immune system of an animal may become compromised due to factors such as exposure to disease and etiologic agents. Furthermore, conditions such as crowded pens and unsanitary structures are often used to house non-human animals. As a result of such conditions, animals are at a high risk of infection and re-infection and of immune system disorders. When animals become immunocompromised in this manner, the ability of the T cells to destroy invading pathogens is reduced, and in severe cases, may be lost altogether. In addition, even when an animal has a functional immune system, the ability of the T cells to resist infection by certain pathogens may be insufficient.

As stated above, widespread usage of antibiotics in the poultry industry has caused increased concern in recent years that antibiotic-resistant strains of bacteria and parasites may develop and spread. Accordingly, it is desired to provide a compound that stimulates the natural immune system of a host animal, thereby enabling the host animal to increase its resistance to infection. In addition, it is desired to provide a compound that affords an alternative to the use of antibiotics. A class of drugs known as immunopotentiators acts on the immune system by priming the function of leukocytes, thereby enabling leukocytes to respond with increased activity upon stimulation by a pathogen. These drugs, when introduced into the body of a host animal, selectively stimulate the natural immune system of the host, thereby reducing or eliminating altogether the necessity to introduce antibiotics into the host's body in order to fight certain infectious agents. As a result of this selective stimulation, i.e., T-cell blastogenesis and production of cytokines, the natural immune system of the host animal achieves an enhanced ability to control the pathogen.

An immunopotentiator, the mushroom lectin FFrL, is provided. While the mechanism of action of the immunopotentiator in the present application is not defined, a blastogenic effect on the T cells is seen after treatment with FFrL. The release of cytokines and their effect on other T cells and other cells of the immune system results in the control or elimination of the pathogens responsible for coccidiosis.

Recent research with other mushroom and mushroom polysaccharide extracts has shown in vivo protective effects against *E. tenella* infection (Guo et al. 2004 and 2005, supra).

The mushrooms and their polysaccharide extracts showed promise in altering bacterial activities and composition in chicken ceca. In normal broilers, the polysaccharide extracts showed a slightly significant effect on growth performance but did not affect weights of immune and gut organs. However, the polysaccharide extracts significantly affected body growth, immune responses, and growth of immune organs and development of gut fragments in coccidian-infected chickens, particularly when the extracts were used in conjunction with vaccine. It was concluded from these studies that supplementing the poultry diet with mushroom and/or herb extracts resulted in enhancement of host innate immunity to pathogens and increased resistance to E. tenella. The increase in resistance was thought to result from enhancement of both the cellular and the humoral immune responses directed against E. tenella in chickens. Indeed, the improved resistance to coccidiosis could be due to non-specific as well specific immunoenhancement exerted by the injected mushroom lectin, resulting in improved innate and adaptive immune responses.

F. fraxinea is a wood-rotting basidiomycetous fungus growing most frequently on the tree stumps of Robinia pseudoacacia. It is a very common wild mushroom widely distributed in Korea and other Asian countries as well as other countries including the USA. The mushroom extract of the invention contains a lectin that is usually prepared under much less stringent conditions than previous studies, i.e., extraction processes for polysaccharides, thus making it more feasible to be produced commercially. Further, the lectin is coupled with successful in ovo delivery, thus offering a promising means of controlling coccidiosis.

Growth performance of E. acervulina-infected chickens is significantly improved by injecting the FFrL into 18-day-old embryos as demonstrated by the higher weight gains observed as compared to infected control birds. FFrL-treated chickens also showed significantly reduced oocyst shedding after oral challenge infection with live parasites, an indication of improved resistance to coccidiosis. In view of the increased evidence that mushrooms and mushroom-derived lectin enhance innate immunity in poultry, characterization of the mechanism of their action at cellular and molecular levels will be determined to elucidate their role as immunopotentiators in poultry and other livestock.

The term "lectin" as used herein refers to a large group of different proteins widely distributed in nature which have the ability to agglutinate erythrocytes and many other types of cells. The term lectin is now generally recognized as designating a "sugar-binding protein or glycoprotein of non-immune origin which agglutinates cells and/or precipitates glycoconjugates" (Goldstein et al. 1980. Nature 285:66). Nearly all lectins can be bound and inhibited by free oligosaccharides or monosaccharides of appropriate specificity (formulation and structure).

The terms "immunopotentiator", "immunopotentiating agent" and "immunopotentiating compound" as used herein, include, but are not limited to an agent or a compound capable of stimulating, enhancing or potentiating normal immune function, or restoring, stimulating, enhancing or potentiating a depressed immune function, or both. "Immunopotentiate" and "immunostimulate" are thus used interchangeably, as are "immunopotentiators" and "immunostimulators", and "immunopotentiating" and "immunostimulating". The immunopotentiators possess pharmacological activity, that is, they are immunostimulatory agents that broadly enhance the immune response of a host leading to nonspecific immunity, for prophylaxis and defense, or they lead to the development of an increased specific immune response to an antigenic material already present in a host, for improved therapy in case of a preexisting disease. Immunopotentiators can increase the degree of the response of the immune system without modifying the nature thereof (for example: increase the amount of antibodies produced), modify the nature of the response of the immune system to the administration of the antigen (for example, induce a cellular response, whereas the administration of the antigen alone caused only a humoral response), and induce or increase the production of cytokines, or of certain cytokines in particular. Immunostimulation has been described in detail, for example, by Chudid et al 1980. In Immunstimulation, Springer Verlag, Heidelberg, N.Y.; Heidelberger, M. 1982. Fortschritte d. Chem. Org. Naturst. 42: 287-298; Drews, J. 1985. Infection 13(Suppl 2):S241-50.

The terms "effective amount" and "effective immunopotentiating amount" of a compound refer to the amount of that compound that will restore immune function to near normal levels, or increase immune function above normal levels in order to control or reduce infection.

Poultry as the term is used herein refers to one or a plurality of game or domesticated birds for use as food, such as chickens, turkeys, geese, ducks, guinea fowl, quail, pheasants, ratites (flightless birds), etc. It will be noted that the financial loss from coccidiosis is greater in chickens than with other domestic birds; however, turkeys, geese, ducks, and guinea fowl also experience coccidiosis losses. Disastrous outbreaks of renal coccidiosis in geese have frequently been recorded. Young pigeons suffer severe mortality rates after acute attacks of diarrhea caused by coccidial infections. Coccidiosis has also produced serious losses in pheasant and quail raised in captivity. The methods of the present invention are also useful for preventing disease in exotic and domesticated pet birds; thus the general term poultry is meant to encompass those birds as well.

As coccidiosis is caused by several apicomplexan parasites of the genus Eimeria, the control mechanisms of the invention are targeted to all Eimeria species, particularly those that are the most common pathogenic species for chickens, namely E. tenella, E. acervulina, and E. maxima.

Also part of this invention is a composition that comprises the lectin FFrL or the FFrL-containing extract, i.e., crude extract, and a carrier, preferably a biologically-acceptable carrier. Typical carriers are aqueous carriers such as water, buffered aqueous solutions, aqueous alcoholic mixtures, and the like. Compositions comprising carriers that are for pharmaceutical use comprise a carrier that is pharmaceutically- or veterinarilly-acceptable. Examples of such carriers are known in the art and need therefore not be provided herein.

The lectin FFrL or the FFrL-containing extract, i.e., crude extract, is preferably suspended in a diluent. A preferred diluent for suspending FFrL, or the crude FFrL extract, is normal, also referred to as "physiological," saline solution. It should be appreciated that other diluents capable of suspending the FFrL for administration into chicks could be utilized in accordance with the present invention. The lectin FFrL or the FFrL-containing extract, i.e., crude extract, can also be given diluted with other immunopotentiating agents or adjuvants; these include cytokines, probiotics, and oligodeoxynucleotides.

Alternatively, a variety of materials can be added to a diluent in accordance with the present invention depending on the requirements of the chicks. For example antibiotics (e.g., gentamicin, ceftiofur, and erythromycin), vaccines (e.g., Marek's Disease vaccine, Infectious Bursal Disease vaccine), vitamins, growth media (tryptose phosphate), meat digests, and/or food colorings may be added to a diluent in accordance with the present invention.

The purified FFrL or FFrL-containing extract, i.e., crude extract, is preferably suspended in a normal saline diluent at about 0.5 mg to about 10 mg dried weight per milliliter of diluent. It will be appreciated that other initial concentrations of the FFrL suspension, or of the suspension of the crude FFrL extract, are within the scope of the present invention because the actual administration to the chick is preferably adjusted and further diluted with a diluent for optimum dosages. The optimum dosage for administration of the FFrL suspension, or of the suspension of the crude FFrL extract, depends upon the different modes of administration, which will be described in more detail herein below, and also on the amount of FFrL suspension, or of the suspension of the crude FFrL extract, hereinafter the "effective amount," which results in stimulation of the immune system such that the effects of coccidiosis, including deaths, intestinal lesions, and weight loss, are reduced.

For example, in one preferred mode of administration, the FFrL suspension, or the suspension of the crude FFrL extract, is administered to the chick at a concentration of about 50 μg/mL. Those of skill in the art will appreciate that the starting concentration of the FFrL-containing suspension is simply diluted with the same diluent in which the FFrL was originally suspended until a desired final dose is realized.

In a preferred method of the present invention, the FFrL suspension, or the suspension of the crude FFrL extract, is administered to the chick in ovo during the embryonic development period. The results of in ovo administration of the FFrL-containing suspension illustrate that this is an effective method to stimulate non-specific cell-mediated immune response and prevent coccidiosis disease in chicks. See, e.g., Example 3, below.

To perform the in ovo method of the present invention, the FFrL or the crude FFrL extract, is preferably suspended in a diluent solution such as described hereinabove. A preferred diluent solution is physiological saline.

An effective amount of the FFrL suspension, or the suspension of the crude FFrL extract, is then administered to chicks in ovo. The preferred developmental stage for administration to chicks in ovo ranges from about day 14 to immediately prior to hatching at about day 21. A more preferred developmental stage ranges from about day 17 to about day 19. The most preferred developmental stage for administration in ovo is at about day 18, when embryonated eggs are transferred from incubators to hatchers and no extra handling is required.

A preferred dose for in ovo administration is about 0.1 mL of the FFrL suspension or the suspension of the crude FFrL extract, at a range from about 50 μg/egg to about 150 μg/egg. A more preferred dose for in ovo administration is about 0.1 mL of the FFrL suspension or the suspension of the crude FFrL extract, at a range from about 75 μg/egg to about 125 μg/egg. A most preferred dose for in ovo administration is about 0.1 mL of the FFrL suspension or the suspension of the crude FFrL extract, at dose of about 100 μg/egg.

The FFrL suspension or the suspension of the crude FFrL extract is preferably injected through the large end of the egg at about one inch into the chorioallantoic membrane. Injection in ovo is preferably carried out under aseptic conditions.

In an alternate embodiment of the in ovo administration method described above, an added step of vaccinating the chick with an anticoccidial vaccine and/or vaccines against other diseases of poultry is performed.

In one embodiment, vaccination is performed simultaneously with the in ovo administration of the FFrL suspension or the suspension of the crude FFrL extract. Alternatively, the vaccination is performed through oral administration following hatching of the chicks such at day zero, day one, and/or beyond.

In an alternative method of the present invention, an effective amount of the FFrL suspension or the suspension of the crude FFrL extract, such as that described herein above is administered to hatched chicks. The preferred age for hatched chicks ranges from immediately post-hatching to about one week old. A more preferred age for hatched chicks ranges from about day zero to about three days old. The most preferred age for hatched chicks is about one day old.

A preferred dose in accordance with the method of the present invention is about 0.1 mL of the FFrL suspension or the suspension of the crude FFrL extract, at a range from about 5 μg/chick to about 160 μg/chick. A more preferred dose in accordance with the method of the present invention is about 0.1 mL of the FFrL suspension or the suspension of the crude FFrL extract, at a range from about 15 μg/chick to about 35 μg/chick. A most preferred dose in accordance with the method of the present invention is about 0.1 mL of the FFrL suspension or the suspension of the crude FFrL extract, at a dose of about 20 μg/chick.

The preferred mode of administration of the FFrL suspension or the suspension of the crude FFrL extract, for hatched chicks is via intraperitoneal injection. Alternatively, the FFrL suspension or the suspension of the crude FFrL extract, is administered to hatched chicks via subcutaneous injection in a method substantially similar to that described hereinabove.

In an alternate embodiment of the present invention, the method described above includes an additional vaccination step. For example, the hatched chicks are preferably vaccinated against coccidiosis via oral administration of an anticoccidial vaccine. One example of such a vaccine is IMMU-COXRTM. anticoccidial vaccine available from Vetech Laboratories. Alternatively, COCCIVACRTM. anticoccidial vaccine by Schering-Plough, or other commercial or autogenous vaccine is utilized. Alternatively, coccidial antigen may be utilized. It will also be appreciated that vaccines against other poultry diseases may be utilized in accordance with the method of the present invention. Any of the aforementioned vaccines can be provided to the chick in ovo or post hatch.

In one embodiment of the present invention, the vaccination step is performed following administration of the FFrL suspension or the suspension of the crude FFrL extract. For example, the vaccination is administered via the food supply to the chicks at the age of about day three and beyond. Alternatively, the vaccine is incorporated into the food supply from day zero. Alternatively, the vaccine is administered simultaneously with the FFrL suspension or the suspension of the crude FFrL extract.

In an alternate embodiment of the method of the present invention, the purified FFrL or FFrL-containing extract, i.e., crude extract, is suspended in a diluent solution such as described hereinabove and administered to hatched chicks via an eye spray. The eye spray administration method does not cause the pain and stress to older chicks associated with conventional inoculation techniques. As the term is used herein, eye spray is synonymous with "in-house" spray, which is known by those of skill in the art to be used with older chicks.

The preferred time period during which eye spray is administered to chicks ranges from immediately after hatching to about four weeks or older. A more preferred time period ranges from about one day to about three weeks old.

A preferred dose for eye spray administration is the FFrL suspension or the suspension of the crude FFrL extract, at a range from about 2 μg/chick to about 16 μg/chick. A more preferred dose for eye spray administration is the FFrL suspension or the suspension of the crude FFrL extract, at a range from about 6 μg/chick to about 10 μg/chick. A most preferred dose for eye spray administration is FFrL suspension or the suspension of the crude FFrL extract, at dose of about 8 μg/chick.

In an alternate embodiment of the eye spray administration method described above, an added step of vaccinating the chick with an anticoccidial vaccine and/or a vaccines against other diseases of poultry is performed.

In one embodiment, vaccination is performed at approximately the same time as the eye spray administration of the FFrL suspension or the suspension of the crude FFrL extract. Alternatively, the vaccination is performed through oral administration following hatching of the chicks such as at day zero, day one, and/or beyond.

The immunopotentiator compounds of the present invention have been found to enhance the blastogenesis of peripheral blood T lymphocytes derived from avian, bovine, porcine, canine and non-human primates in vitro. Some of the immunopotentiator compounds used in the present invention have been found to be active in vitro at concentrations as low as 1 μg/ml. In many cases, the compounds are non-cytotoxic in vitro at concentrations up to 100 μg/ml, and in some cases, up to 1 mg/ml. Many compounds have been found to provide a rapid blastogenic response in vitro within 72 hours, and some have provided this response within 48 hours.

EXAMPLES

Having now generally described this invention, the same will be better understood by reference to certain specific examples, which are included herein only to further illustrate the invention and are not intended to limit the scope of the invention as defined by the claims.

Example 1

Preparation and Biological Activity of Crude FFrL

The carpophores of *F. fraxinea* were collected at Cheonggye Mountain in Gyung-Ki Province, South Korea, and kept frozen at −70° C. until use. Two kilograms of the frozen fruiting bodies were homogenized in 20 L of 20 mM Tris-HCl buffer (pH 8.0) with an Osterizer blender and then extracted for 18 h at 4° C. with frequent gentle swirling. The resulting suspension was filtered, and ammonium sulfate was added to the filtrate to 50% saturation. After standing overnight at 4° C., the resulting precipitate was separated by centrifugation at 8,000 g and 4° C. for 20 min. The supernatant was collected and more ammonium sulfate was added to the supernatant to obtain 100% saturation. After standing overnight at 4° C., the resulting precipitate (from the second ammonium sulfate precipitation) was separated by centrifugation at 8,000 g and 4° C. for 20 min. The precipitate was dissolved in 50 mM NaCl, 50 mM Tris-HCl buffer (pH 8.0), dialyzed against distilled water for 5-7 days at 4° C. with frequent changing of distilled water. After dialysis, the dialysate was freeze-dried to yield crude FFrL, a grayish brown amorphous powder freely soluble in distilled water as well as saline and tissue culture media (e.g., RPMI 1640) but is not soluble in organic solvents such as ethanol, acetone, chloroform or diethyl ether. Downstream purification yields more active FFrL as verified by its ability to agglutinate erythrocytes of BALB/c mice.

FFrL activity was verified by its ability to agglutinate BALB/c erythrocytes (Table 1). Downstream purification of FFrL using different HPLC methods (two different ion-exchange column chromatography methods and one gel filtration method) resulted in a 64-fold purification with a 22.1% yield; however, only crude FFrL is reported in this study. The lyophilized extract, crude FFrL, was dissolved in 20 mM Tris-HCl buffer (pH 8.0) and applied on a DEAE-cellulose column (2.5 cm×20 cm; Sigma, USA) and eluted with the same buffer. Each fraction was assessed for hemmagglutinating activity as described below. The hemmagglutinating fractions were pooled, dialyzed against 20 mM Tris-HCl buffer (pH 8.0), and then loaded onto a DEAE-Sephacel column equilibrated with 20 mM Tris-HCl buffer (pH 8.0). The bound components were eluted with a linear gradient of 0-0.4 mol/L NaCl in 20 mM Tris-HCl buffer (pH 8.0). The active fractions were pooled and further purified with gel filtration on a Sephacryl S-200 HR column (1.0 cm×90 cm; Sigma). The purified lectin fractions were pooled, dialyzed against distilled water and then lyophilized, giving a purified lectin FFrL.

Hemagglutination test. In the assay for hemmagglutinating activity, a serial two-fold dilution of the lectin solution in microtiter U-plates (20 μl) was mixed with 30 μl of a 2% suspension of ICR mouse red blood cells in phosphate buffered saline (pH 7.2) at 37° C. The results were read after 30 min. The hemmagglutinating titer, defined as the reciprocal of the higher dilution exhibiting hemagglutination, was reckoned as one hemagglutination unit. It is noteworthy that when tested on several cell types, crude FFrL agglutinated not only the erythrocytes of BALB/c mice, but also various other cells including thymocytes of BALB/c mice, erythrocytes of Sprague-Dawley rats, mouse RAW 264.7 cells, mouse sarcoma 180 cells, human THP-1 cells, and human cervical carcinoma HeLa cells (unpublished data). However, crude FFrL did not agglutinate human A, B, AB, or O erythrocytes.

TABLE 1

Purification and hemmagglutinating activity of *F. fraxinea*-derived lectin, FFrL

| Purification Step | Total Protein (mg) | Specific Activity (U/mg)* | Total Activity (U) | Fold Purification[#] | Recovery (%) |
|---|---|---|---|---|---|
| Crude FFrL | 3,039.0 | 64 | 194,496 | 1 | 100.0 |
| DEAE-cellulose | 279.5 | 256 | 71,552 | 4 | 36.8 |
| DEAE-Sephacel | 171.1 | 256 | 43,801 | 8 | 22.5 |
| S200-HR | 10.5 | 4,096 | 43,008 | 64 | 22.1 |

*Upon purification, FFrL activity was verified by its ability to agglutinate BALB/c erythrocytes as described in the text and calculated as the inverse of the minimum concentration producing a positive reaction in the hemagglutination assay.

[#]The purification steps resulted in a 64-fold purification with a 22.1% yield.

Example 2

Mitogenic Activities on Chicken Splenic Lymphocytes

The mitogenic activity of FFrL on the splenic lymphocytes of chickens was measured by the non-radioactive, enzymatic XTT assay (Okamura et al. 2003. *Avian Dis.* 47:1331-1338; Roehm et al. 1991. *J. Immunol. Methods* 142: 257-265). Spleen cells were prepared as described by Dalloul et al. (2002. *Poult. Sci.* 81:1509-1515) and co-cultured with varying concentrations (0, 1.56, 3.13, 6.25, 12.5, and 25 μg/mL) of either FFrL or concanavalin A (ConA) as positive control. Cells were cultured in a 5% $CO_2$ atmosphere at 41° C. for 48 h; cell growth was then assessed by the XTT calorimetric method following either a three or a five hour reaction.

As depicted in FIG. 1, FFrL showed a potent mitogenic activity against spleen lymphocytes, especially at lower concentrations, where crude FFrL exerted stronger mitogenic activity than ConA, a well-known potent T lymphocyte mitogen.

Example 3

Induction of Nitric Oxide Production in Macrophages

Induction of nitric oxide production was assayed using the chicken macrophage cell line HD11 stimulated by FFrL and controls. Cells were cultured in 96-well plates at a concentration of $1\times10^5$/well (100 µL) and stimulated with 100 µL media (negative control), recombinant chicken interferon-gamma expressed in COS-7 cells ($IFN_\gamma$; positive control), or varying concentrations of FFrL (12.5, 25.0, 50.0, or 100.0 µg/mL). Cells were cultured in a 5% $CO_2$ atmosphere at 41° C. for 24 h and nitric oxide was assessed in triplicate wells as nitrite content in conditioned media using Griess reagent as described (Ding et al. 1988; Lillehoj et al. 2004. *Avian Dis.* 48: 244-253). Mean nitrite values were calculated using a sodium nitrite standard curve.

Figure 2:
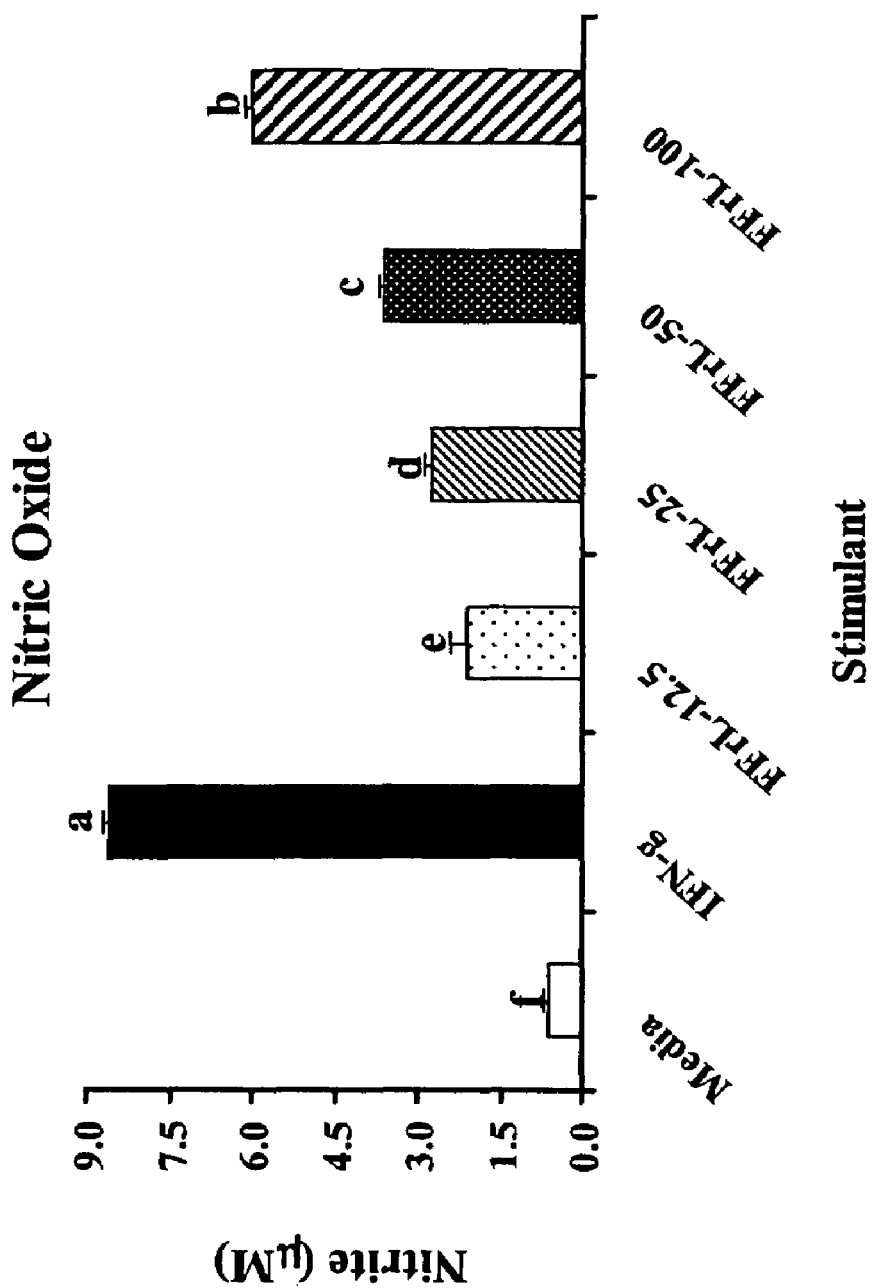
FIG. 2 depicts nitric oxide secretion (μM) by HD11 cells 24 h following IFN-γ or FFrL stimulation. Cells were cultured in 96-well plates at a concentration of 1×10$^5$/well (100 μL) and an equal volume of appropriate controls and FFrL added at multiple concentrations (μg/mL). Supernatants (100 μL) of activated cells were transferred to new 96-well plates (triplicate), 100 μL Griess reagent added, and the optical density read at 540 nm. $^{a-f}$ P<0.05; error bars=SE.

FFrL significantly induced (P<0.05) nitric oxide secretion in HD11 cells in a dose-dependent fashion (FIG. 2).

Example 4

Suppression of Tumor Cells

The LSCC-RP9 B lymphoblastoid cell line was used to test the anti-tumor activity of FFrL. RP9 cells ($5\times10^4$/well of 96-well plates) were cultured with 100 µL of media as a negative control, human recombinant $TNF_\alpha$ as a positive control (3 µg/mL; R & D System, Minneapolis, Minn.), or increasing concentration of FFrL (12.5, 25.0, 50.0, or 100.0 µg/mL). Cultures were incubated in a 5% $CO_2$ atmosphere at 41° C. for 24 h; cell proliferation was assessed using the WST-8 tetrazolium salt assay (Cell-Counting Kit-8®, Dluindo Molecular Technologies, Inc., Gaithersburg, Md.) as described (Miyamoto et al. 2002. *Avian Dis.* 46: 10-16).

Figure 3:
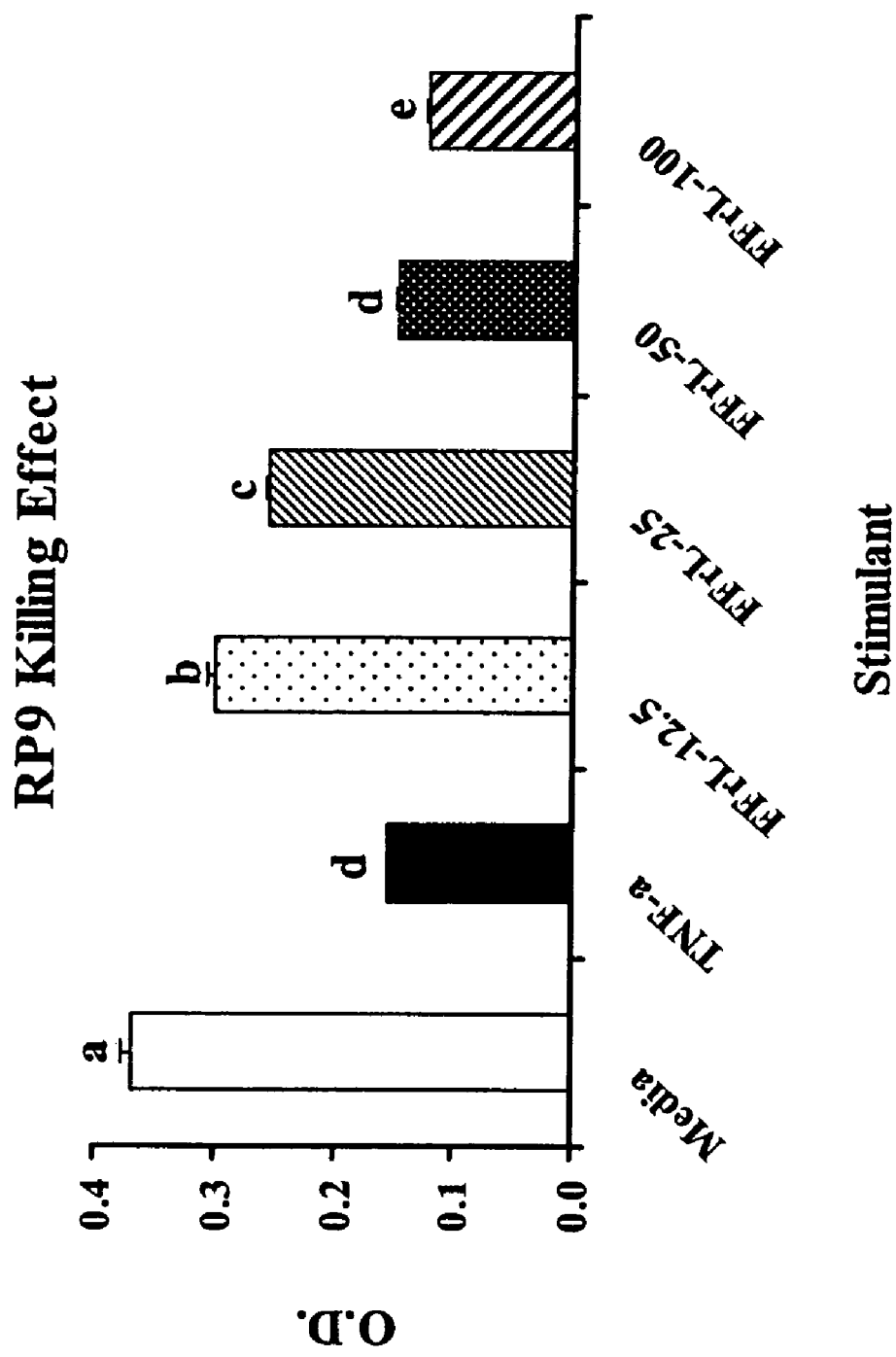
FIG. 3 depicts the effect of FFrL on RP9 proliferation as measured by the WST-8 tetrazolium salt assay. Cells were cultured in 96-well plates at a concentration of 1×10$^5$/well (100 μL) and an equal volume of appropriate controls and FFrL added at multiple concentrations (μg/mL). Following 24 h incubation, 100 μL of activated cells were transferred to new 96-well plates (triplicate); 10 μL of CCK-8® reagent was added to each well. Plates were further incubated for 4 h at similar conditions and the optical density read at 450 nm. $^{a-e}$ P<0.05; error bars=SE.

FFrL significantly suppressed (P<0.05) RP9 cell growth (FIG. 3) in a dose-dependent fashion. The highest FFrL concentration was effective in suppressing RP9 tumor cell growth; it suppressed tumor cell growth more effectively than recombinant human TNF-α (FIG. 3).

Example 5

Protective Effect of FFrL Against Poultry Coccidiosis

Eighteen-day-old specific-pathogen-free chicken embryos (White Leghorn SPAFAS, Charles River Laboratories, Storrs, Conn.) were injected with either PBS (100 µL per egg) as control or FFrL extract (100 µg in 100 µL per egg) using a customized Intelliject® in ovo injection system (AviTech LLC, Hebron, Md.). Birds were hatched at the Animal and Natural Resources Institute (USDA, Beltsville, Md.), wing-tagged, and feed and water were provided ad libitum throughout the experimental period.

One week post hatch, each bird (except the negative control groups) received an oral dose of 10,000 sporulated *Eimeria acervulina* (EA) oocysts. Fecal materials were collected 6-9 days post infection (dpi), processed, and the number of shed oocysts counted as described (Lillehoj and Choi. 1998. *Avian Dis.* 42: 307-314). Oocyst production and shedding were assessed as described by Dalloul et al. (2005, supra). Briefly, collected fecal samples were soaked overnight, ground and homogenized. Two 35-ml samples were taken, diluted, and the oocysts counted microscopically using a McMaster counting chamber (HK Inc., Tokyo, Japan). The number of oocysts per bird was calculated using the formula: total number oocysts=oocyst count×dilution factor×(fecal sample volume/counting chamber volume)/number of birds per cage. All birds were individually weighed before and nine days post infection.

Figure 4A:
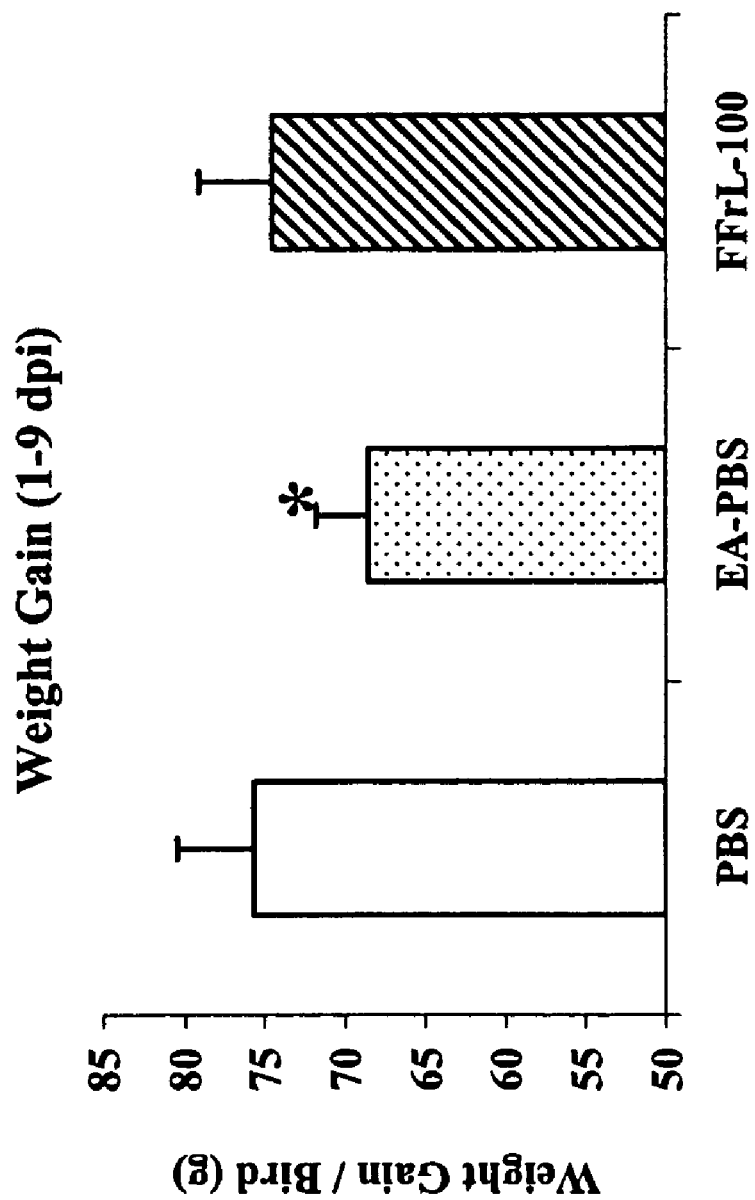
FIGS. 4A and B depict body weight gains during *E. acervulina* infection. Embryos (18 days old, n=15/group) were injected into the amniotic cavity with either PBS (100 μL) or crude FFrL lectin (100 μg/100 μL) using an in ovo injector. Hatched chicks (n=12-15/group) were inoculated with 10,000 *E. acervulina* oocysts at 6 days of age. Birds were individually weighed on 1 and 9 dpi and both weight gain (FIG. 4A) and percent gain (FIG. 4B) were statistically analyzed by ANOVA and the Tukey-Kramer post hoc test. An asterisk (*) indicates significantly (P<0.05) different than the infected controls (EA-PBS); error bars=SE.
Figure 4B:
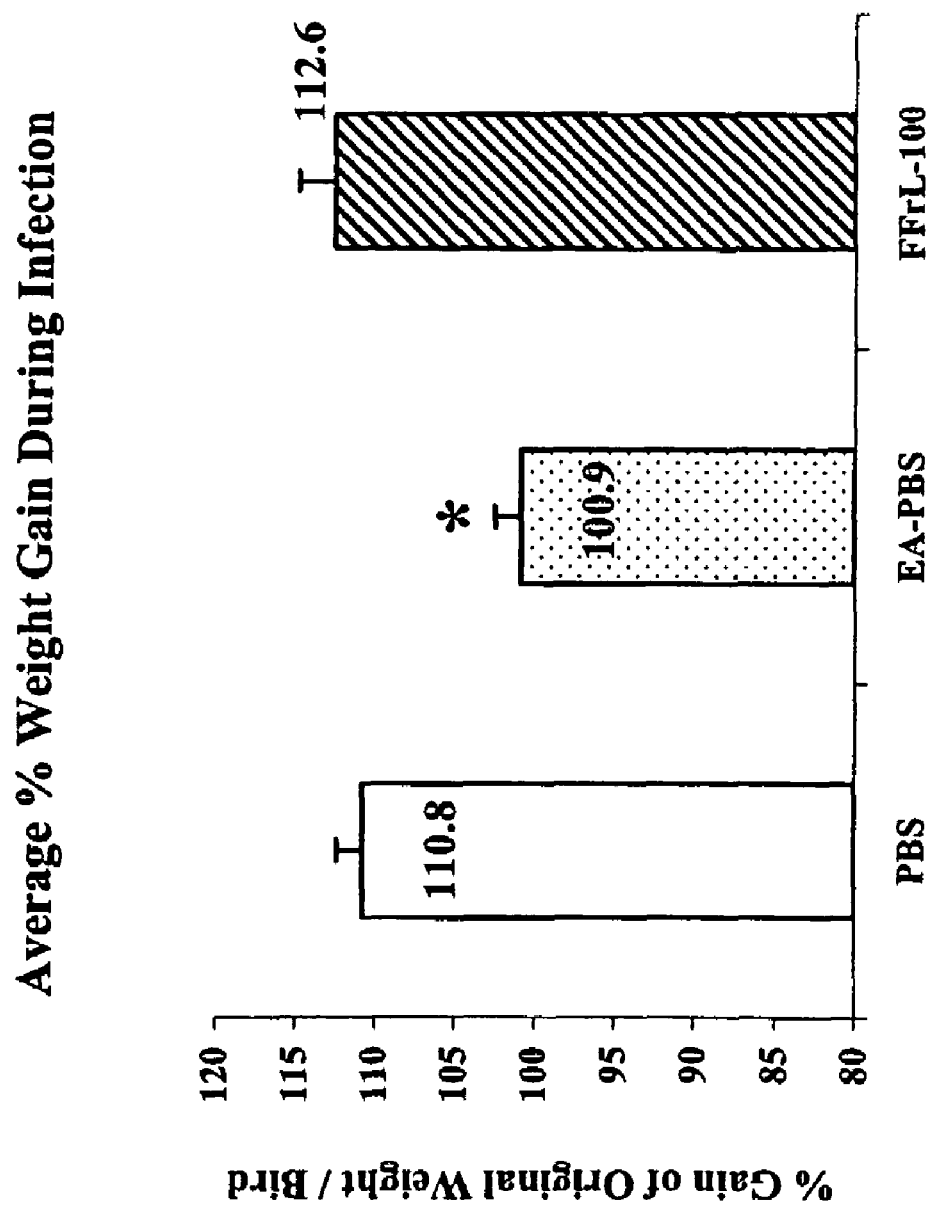
Figure 5:
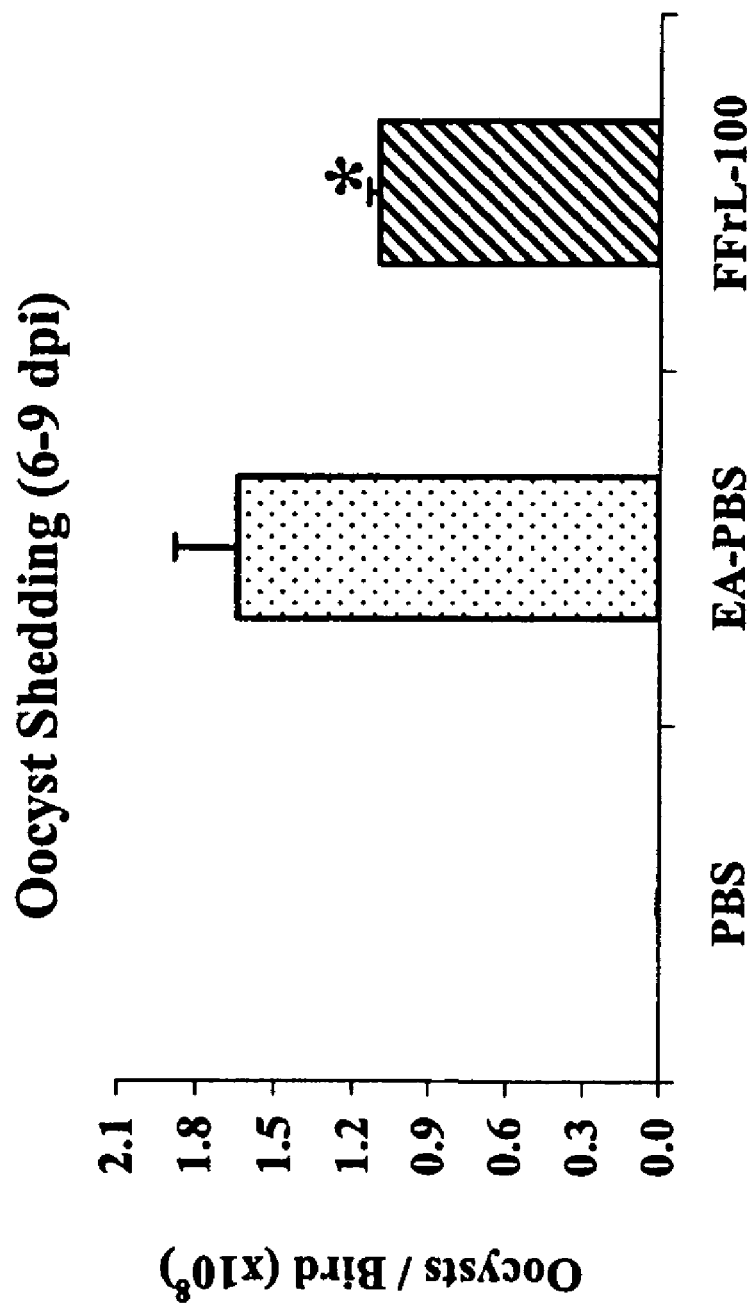
FIG. 5 depicts oocyst shedding by chicks 6-9 days following *E. acervulina* infection. Embryos (18 days old, n=15/group) were injected into the amniotic cavity with either PBS (100 μL) or crude FFrL lectin (100 μg/100 μL) using an in ovo injector, and hatched chicks (n=12-15/group) were inoculated with 10,000 *E. acervulina* oocysts at 6 days of age. Fecal materials were collected from days 6 to 9 post infection, processed and shed oocysts counted. An asterisk (*) indicates significantly (P<0.05) different than the infected controls (EA-PBS); error bars=SE.

Body weight gains and fecal oocyst shedding were evaluated during the infection period. FFrL-treated chickens showed significantly higher weight gains (P<0.05) than infected controls (FIG. 4A), and similar weight gains to those of normal non-infected chickens. The percent body weight gain per bird was also computed and one-way ANOVA applied as described earlier (FIG. 4B). Percent body weight gain was significantly lower (P=0.003) in the infected control group (EA-PBS) as compared to either the non-infected (PBS) or the FFrL-injected, infected (EA-FFrL) groups. No differences (P>0.05) were found between the non-infected (PBS) and the FFrL-injected (FFrL) groups. Furthermore, FFrL injection of embryos also resulted in significantly lower fecal oocyst shedding as compared to PBS-injected birds following *E. acervulina* challenge (FIG. 5).

Statistical Analysis: Differences between experimental treatments were tested by one-way ANOVA (InStat®, Graph-Pad Software Inc., San Diego, Calif.) and were considered significant at P<0.05 by the Tukey-Kramer Multiple Comparisons Test. An asterisk in the figures indicates significant differences as compared to the positive control (PBS-injected and *Eimeria*-infected).

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

I claim:

1. A method for stimulating a non-specific cell-mediated immune response in poultry comprising the steps of:
    (a) obtaining a solution comprising FFrL (Fomitella fraxinea lectin) suspended in a diluent; and
    (b) administering to said poultry via in ovo inoculation an amount of said solution effective to reduce the output of *Eimeria* oocysts and to improve weight gain in chickens given said inoculation as compared to chickens not inoculated in ovo.

2. A method for stimulating a non-specific cell-mediated immune response in poultry and thereby augmenting a response to a conventional anticoccidial vaccine comprising the steps of the method as recited in claim 1, and further comprising the step of vaccinating said poultry with a conventional anticoccidial vaccine.

3. The method as recited in claim 2, wherein said anticoccidial vaccine is administered to said poultry simultaneously with the administration of said FFrL solution.

4. The method as recited in claim 2 wherein said anticoccidial vaccine is administered to said poultry following the administration of said FFrL solution.

5. The method as recited in claim 4, wherein said anticoccidial vaccine is administered to said poultry at the age of about day one.

6. The method as recited in claim 2, wherein said FFrL solution is administered to said poultry in ovo at least once during a period of time from about day 14 to immediately prior to hatching.

7. A method for stimulating a non-specific cell-mediated immune response in poultry comprising the steps of:
   (a) obtaining a solution comprising FFrL suspended in a diluent; and
   (b) administering to said poultry following the hatching thereof an intraperitoneal injection of an amount of said solution effective to reduce the output of *Eimeria* oocysts and to improve weight gain in chickens given said injection as compared to chickens not injected intraperitoneally.

8. A method for stimulating a non-specific cell-mediated immune response in poultry and thereby augmenting a response to a conventional anticoccidial vaccine comprising the steps of the method as recited in claim 7, and further comprising the step of vaccinating said poultry with a conventional anticoccidial vaccine.

9. A method for stimulating a non-specific cell-mediated immune response in poultry comprising the steps of:
   (a) obtaining a solution comprising FFrL suspended in a diluent; and
   (b) administering to said poultry following the hatching thereof an subcutaneous injection of an amount of said solution effective to reduce the output of *Eimeria* oocysts and to improve weight gain in chickens given said injection as compared to chickens not given a subcutaneous injection.

10. A method for stimulating a non-specific cell-mediated immune response in poultry and thereby augmenting a response to a conventional anticoccidial vaccine comprising the steps of the method as recited in claim 9, and further comprising the step of vaccinating said poultry with a conventional anticoccidial vaccine.

11. A method for stimulating a non-specific cell-mediated immune response in poultry comprising the steps of:
   (a) obtaining a solution comprising FFrL suspended in a diluent; and
   (b) administering to said poultry following the hatching thereof an amount of said solution, via an eye spray, effective to reduce the output of *Eimeria* oocysts and to improve weight gain in chickens given said solution as compared to chickens not given the solution.

12. A method for stimulating a non-specific cell-mediated immune response in poultry and thereby augmenting a response to a conventional anticoccidial vaccine comprising the steps of the method as recited in claim 11, and further comprising the step of vaccinating said poultry with a conventional anticoccidial vaccine.

* * * * *